United States Patent
Gygax

Patent Number: 5,457,226
Date of Patent: Oct. 10, 1995

[54] PROCESS FOR THE MANUFACTURE OF CINNAMIC ACID DERIVATIVES

[75] Inventor: Peter Gygax, Fällanden, Switzerland

[73] Assignee: Givaudan-Roure Corporation, Clifton, N.J.

[21] Appl. No.: 232,131
[22] PCT Filed: Aug. 27, 1993
[86] PCT No.: PCT/EP93/02317
§ 371 Date: Apr. 28, 1994
§ 102(e) Date: Apr. 28, 1994
[87] PCT Pub. No.: WO94/05621
PCT Pub. Date: Mar. 17, 1994

[30] Foreign Application Priority Data

Sep. 3, 1992 [CH] Switzerland ............... 2771/92
Jul. 23, 1993 [EP] European Pat. Off. ....... 93111812

[51] Int. Cl.⁶ .................................... C07C 69/76
[52] U.S. Cl. ................... 560/75; 560/55; 502/478; 502/465
[58] Field of Search ............ 560/75, 55; 562/465, 562/478

[56] References Cited

U.S. PATENT DOCUMENTS 4,970,332  11/1990  Caskey .................... 560/104

FOREIGN PATENT DOCUMENTS

0509462A2  10/1992  European Pat. Off..
WO/10617   9/1990   WIPO.

OTHER PUBLICATIONS

R. F. Heck, "Organic Reactions" Textbook, vol. 27, Chapter 2, pp. 345–389 (1982).

Primary Examiner—Paul J. Killos
Attorney, Agent, or Firm—George M. Gould; George W. Johnston; Mark E. Waddell

[57] ABSTRACT

A novel process for the manufacture of a cinnamic acid derivative of the formula

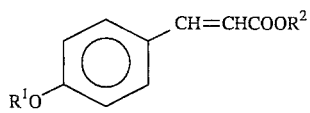

wherein $R^1$ signifies hydrogen or $C_{1-8}$-alkyl and $R^2$ signifies hydrogen, $C_{1-10}$-alkyl, $C_{1-10}$-hydroxyalkyl or $C_{1-4}$-alkoxy-$C_{1-10}$-alkyl, is described in which a 4-$R^1$O-halobenzene is reacted with acrylic add or an acrylic acid ester $CH_2$=CHCOOR$^2$ using a heterogeneous palladium catalyst in the presence of the alkanoic acid ammonium salt formed from a $C_{2-5}$-alkanoic acid and an aliphatic mono-, di- or trialkylamine or heterocyclic amine. In the case of the manufacture of the cinnamic acid derivative I in which $R^2$ signifies hydrogen, the reaction can be carried out in the presence of the amine in place of the alkanoic acid ammonium salt. A further aspect of the described invention comprises reacting the 4-$R^1$O-iodobenzene with the product of the Michael addition of an acrylic acid ester $CH_2$=CHCOOR$^{2'}$, wherein $R^{2'}$ has the above significance of $R^2$ except hydrogen, with an aliphatic or heterocyclic primary of secondary amine using a heterogeneous palladium catalyst and in the presence of a $C_{2-5}$-alkanoic add in order to manufacture the above cinnamic add derivatives with the exception of the substituted cinnamic acid itself.

In view of their UV-B absorbing properties the thus-manufactured cinnamic acid derivatives are suitable as UV-B filters for cosmetic agents, e.g. sunscreen agents.

11 Claims, No Drawings

PROCESS FOR THE MANUFACTURE OF CINNAMIC ACID DERIVATIVES

This application is a 371 of PCT/EP93/02317 Aug. 27, 1993.

The present invention is concerned with the manufacture of cinnamic acid derivatives which, owing to their UV-B absorbing properties, are suitable as UV-B filters for cosmetic agents, e.g. sunscreen agents.

R. F. Heck in Org. Reactions, vol. 27, chapter 2, pages 345–389 (1982) describes, inter alia, the preparation of cinnamic acid derivatives by reacting haloaromatics with acrylic acid derivatives in the presence of palladium compounds as homogeneous catalysts and of bases, e.g. secondary or tertiary amines. Disadvantages of this reaction are, that the for the most part expensive homogeneous palladium catalysts can not be recovered in a simple manner after the reaction and that the reaction time is relatively long. For example, a 68 percent yield of methyl pmethoxycinnamate is achieved after 5 hours when p-iodoanisole is vinylated with methyl acrylate in the presence of palladium acetate and tri(n-butyl)amine [see also R. F. Heck and J. P. Nolley, Jr., J. Org. Chem. 37, 2310 (1972)].

U.S. Pat. No. 4,970,332 also describes the reaction of piodoanisole (and other palkoxyiodobenzenes) with alkyl acrylates in order to prepare corresponding cinnamic acid derivatives. In this case, the reaction is carried out in the presence of a heterogeneous palladium catalyst (palladium on a carrier material) and a trialkylamine and the palladium catalyst can be recovered by filtration. However, as in the above Heck process, the reaction time is relatively long, for example 2 to 4 hours in the preparation of 2ethylhexyl pmethoxycinnamate. A further disadvantage is that the process is limited to the use of trialkylamines as the bases.

The object of the present invention is to carry out such alkenylations more rapidly, with higher yields and with a wider choice of amines. This object has surprisingly been achieved by carrying out the reaction of the haloaromatic with the acrylic acid derivative inter alia in the presence of an alkanoic acid ammonium salt formed from an alkanoic acid and a primary, secondary or tertiary amine as defined in more detail hereinafter.

The process in accordance with the invention for the manufacture of a cinnamic acid derivative of the general formula

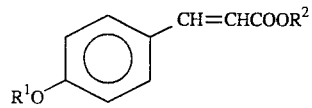   I wherein
$R^1$ signifies hydrogen or $C_{1-8}$-alkyl and
$R^2$ signifies hydrogen, $C_{1-10}$-alkyl, $C_{1-10}$-hydroxyalkyl or $C_{1-4}$-alkoxy-$C_{1-10}$-alkyl,
is characterized by reacting a substituted benzene of the general formula

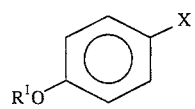   II wherein $R^1$ has the significance given above, and X is iodine, or can also be bromine, when $R^2$ is hydrogen, with acrylic acid or an acrylic acid ester of the general formula $$CH_2=CHCOOR^2 \quad \text{III}$$

wherein $R^2$ has the significance given above, using a heterogeneous palladium catalyst and in the presence of the alkanoic acid ammonium salt formed from a $C_{2-5}$-alkanoic acid and a mono-, di- or trialkylamine of the general formula $$NR^3R^4R^5 \quad \text{IV}$$

wherein
$R^3$ and $R^4$ each independently signify hydrogen or $C_{1-10}$-alkyl and
$R^5$ signifies $C_{1-10}$-alkyl,
or an optionally N-($C_{1-4}$-alkyl)-substituted pyrrolidine, piperidine or morpholine (V), with the proviso that in the case of the manufacture of the cinnamic add derivative of formula I in which $R^2$ signifies hydrogen the reaction can be carried out in the presence of the mono-, di- or trialkylamine of formula IV or of the optionally N-($C_{1-4}$-alkyl)substituted pyrrolidine, piperidine or morpholine (V) in place of the alkanoic acid ammonium salt defined above.

Under the term "alkyl" used in respect of the above formulae I, II, III and IV there are to be understood, depending on the number of carbon atoms, not only straight-chain but also branched-chain alkyl groups. Methyl, ethyl, propyl, isopropyl, n-butyl, isobutyl, tert.butyl, n-pentyl, tert.pentyl, neopentyl, n-hexyl, n-heptyl, 2-ethylhexyl, 1,1,3,3-tetramethylbutyl, n-nonyl and n-decyl are examples of such alkyl groups. The term "alkoxy", as part of the alkoxyalkyl group ($R^2$), signifies such groups in which the alkyl part has the previous significance. Examples of pyrrolidine, piperidine and morpholine, each of which can be N-substituted, are the unsubstituted heterocycles themselves and N-methylpyrrolidine, N-ethylpiperidine and N-methylmorpholine.

As heterogeneous catalysts there especially come into consideration palladium on charcoal, palladium on siliceous earth, palladium on alumina and palladium on barium sulphate; other palladium catalysts of the palladium on carrier material type can, of course, also be used in the process in accordance with the invention. Palladium on charcoal is preferably used as the heterogeneous palladium catalyst.

Although the process in accordance with the invention is ultimately carried out in the presence of, inter alia, one of the alkanoic acid ammonium salts defined above, an excess of the $C_{2-5}$-alkanoic acid or of the primary, secondary or tertiary amine can readily be present in the reaction system. In general, about 0.2 to 10 equivalents of the $C_{2-5}$-alkanoic add per equivalent of the amine, preferably about equivalent amounts of the two reagents, are used in the reaction system in order to produce the alkanoic add ammonium salt, i.e. the salt of the formula $$R^6COO^{\ominus}HN^{\oplus}R^7R^8R^9 \quad \text{VI}$$

wherein
$R^6$ signifies $C_{1-4}$-alkyl and either
$R^7$ and $R^8$ each independently signify hydrogen or $C_{1-10}$-alkyl and
$R^9$ signifies $C_{1-10}$-alkyl or
$R^7$ signifies hydrogen or $C_{1-4}$-alkyl and
$R^8$ and $R^9$ together with the nitrogen atom to which they are attached signify pyrrolidino, piperidino or morpholino,
in situ. However, the reaction of the substituted benzene of formula II with acrylic acid or an acrylic acid ester of formula III can equally be carried out in the presence of an already produced alkanoic acid ammonium salt of formula VI.

Furthermore, the reaction can be carried out in the presence or absence of a solvent, with an aromatic hydrocarbon, e.g. benzene, toluene or a xylene, an aliphatic alcohol, e.g. ethanol or 2-ethylhexanol, or dimethylformamide being a suitable solvent which may be used. When an aliphatic alcohol is used for this purpose, the preferred alcohol is that which corresponds to the optionally substituted alkyl residue $R^2$ of the acrylic acid ester, e.g. 2-ethylhexanol in the reaction of 2-ethylhexyl acrylate. Moreover, the reaction is conveniently carried out at temperatures between about 80° C. and about 200° C., preferably in the temperature range of about 120° C. to about 160° C.

When the process in accordance with the invention is carried out by producing the alkanoic acid ammonium salt of formula VI in situ, the reaction mixture comprising the benzene of formula II, the acrylic acid or the acrylic acid ester of formula III, the heterogeneous palladium catalyst, the $C_{2-5}$-alkanoic acid ($R^6COOH$), the amine ($NR^7R^8R^9$) and optionally solvent can be heated until the reaction has finished. In this case, the molar ratio acid:amine is generally about 1:1 to about 10:1, preferably about 1:1 to about 2:1. Alternatively, the amine $NR^7R^8R^9$ can be added relatively slowly to the rest of the reaction mixture such that finally the molar amount of added amine is in excess compared with the molar amount of $C_{2-5}$-alkanoic acid originally present in the reaction system. The molar ratio acid:amine in this case is generally up to about 1:5. This situation is probably due to the fact that in the reaction between the substituted benzene of formula II and the acrylic acid or the acrylic acid ester of formula III catalysed by the alkanoic acid ammonium salt of formula VI formed in situ the corresponding ammonium iodide and the alkanoic acid are always generated and that the alkanoic acid is then in the position of forming with an additional amount of added amine further alkanoic acid ammonium salt which, in turn, is again implicated for the catalysis of the main reaction. This operates until the main reaction has finished.

As indicated above in the definition of the process in accordance with the invention, the presence of the $C_{2-5}$-alkanoic acid is superfluous when acrylic acid itself is used as the reaction participant of formula III ($R^2$=hydrogen). In this case, the acrylic acid serves as an acid with which the amine IV or V can be reacted to give a suitable carboxylic acid ammonium salt. Such a carboxylic acid ammonium salt (of the formula $CH_2=CHCO^{\ominus}HN^{\oplus}R^7R^8R^9$) positively influences the reaction between the substituted benzene of formula II and the acrylic acid, which in this case is present as the second reaction participant.

The amine IV or V (alternatively amine of the formula $NR^7R^8R^8$) required for the formation of the alkanoic acid ammonium salt or acrylic acid ammonium salt is preferably ethyldiisopropylamine, diethylamine, diisopropylamine or 1,1,3,3-tetramethylbutylamine. The $C_{2-5}$-alkanoic acid ($R^6COOH$) used for the same purpose is preferably acetic acid or propionic acid.

It is known that primary and secondary amines can add to acrylic acid esters in the sense of a Michael addition (see, for example, the article by F. Möller, in Houben-Weyl, Methoden der organischen Chemie, vol. 11/1, pages 267 et seq.). When using the present primary or secondary amines and acrylic acid esters, this proceeds according to the following equation:

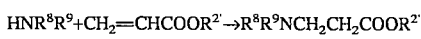

wherein $R^8$ and $R^9$ have the significances given above and $R^{2'}$ signifies $C_{1-10}$-alkyl, $C_{1-10}$- hydroxyalkyl or $C_{1-4}$alkoxy-$C_{1-10}$-alkyl.

It has surprisingly been found that the thus-produced β-aminopropionic acid esters can be reacted with halobenzene or substituted derivatives thereof in the presence of an alkanoic acid and a heterogeneous palladium catalyst to give the corresponding cinnamic acid esters. This represents a further aspect of the present invention which, more precisely, is a process for the manufacture of a cinnamic acid derivative of the general formula

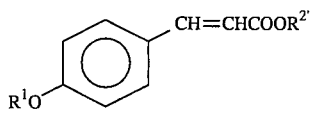

wherein $R^1$ signifies hydrogen or $C_{1-8}$-alkyl and $R^{2'}$ signifies $C_{1-10}$-alkyl, $C_{1-10}$-hydroxyalkyl or $C_{1-4}$-alkoxy $C_{1-10}$-alkyl, characterized by reacting a substituted benzene of the general formula

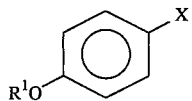

wherein $R^1$ and X have the significance given above, with the product of the Michael addition of an acrylic acid ester of the general formula

wherein $R^{2'}$ has the significance given above, with a primary or secondary amine of the general formula

wherein either
$R^8$ signifies hydrogen or $C_{1-10}$-alkyl and
$R^9$ signifies $C_{1-10}$-alkyl or
$R^8$ and $R^9$ together with the nitrogen atom to which they are attached signify pyrrolidino, piperidino or morpholino, using a heterogeneous palladium catalyst and in the presence of a $C_{2-5}$-alkanoic acid.

The same heterogeneous palladium catalysts as mentioned in connection with the earlier process can be used in this process. The same applies to solvents which may be used and to the suitable reaction temperatures.

The β-aminopropionic acid esters $R^8R^9NCH_2CH_2COOR^{2'}$ can be detected as intermediates in the reaction in accordance with the invention of a substituted benzene of formula II with an acrylic acid ester of formula IIr when primary or secondary amines of formula VII are used. If the temperature is held below about 100° C. at the beginning of the reaction, the formation of the corresponding β-aminopropionic acid ester $R^8R^9NCH_2CH_2COOR^{2'}$ is predominantly observed and this is then converted into the cinnamic acid derivative at elevated temperatures.

The end products, i.e. the cinnamic acid derivatives of formula I or I', can be isolated and purified according to methods known per se.

The starting materials and, respectively, other reaction participants of formulae II–V (including III') and VII are for the most part known compounds or can be produced analogously to the known compounds.

The process in accordance with the invention, irrespective of whether it is carded out using the alkanoic acid ammonium salt, optionally produced in situ, or the β-aminopropionic acid ester $R^8R^9NCH_2CH_2COOR^{2'}$ is preferably carried out using piodoanisole as the compound of formula II and/or 2-ethylhexyl acrylate as the compound of formula III. In the most preferred embodiment the process is directed to the manufacture of 2-ethylhexyl p-methoxycinnamate starting from these two starting materials. This product, which is also known under the trade name Parsol® MCX, as well as the other reaction products have UV-B absorbing properties and are especially suitable as UV-B filters for cosmetic agents, e.g. sunscreen creams and milks, the formulation and use of which are known per se.

The following Examples illustrate the invention.

Example 1

A mixture of 4.68 g (20 mmol) of p-iodoanisole, 4.05 g (22 mmol) of 2-ethylhexyl acrylate, 2.22 g (22 mmol) of triethylamine, 1.32 g (22 mmol) of acetic add and 15 mg of palladium of charcoal (5%) is stirred at 150° C. After one hour it is established by gas chromatography that the reaction has been completed. The mixture is then treated at about 80° C. with water and toluene and the catalyst is filtered off. The organic phase is washed in sequence with 2N hydrochloric acid and water, dried over anhydrous sodium sulphate and concentrated under reduced pressure. After distillation there is obtained pure 2-ethylhexyl p-methoxycinnamate, b.p. about 185° C./0.3 Torr. The yield is 92% of theory. 1H-NMR (CDCl$_3$, 200 MHz): 0.86–0.98 ppm (m, 6H), 1.25–1.72 ppm (m, 9H), 3.84 ppm (s, 3H), 4.11 ppm (d, 6Hz, 2H), 6.32 ppm (d, 15.5 Hz, 1H), 6.85–6.95 ppm (duplettoid m, 1H), 7.44–7.54 ppm (duplettoid m, 1H), 7.64 ppm (d, 15.5 HZ, 1H).

Example 2

The same reaction is carded out analogously to the process described in Example 1, but using 2.84 g (22 mmol) of ethyldiisopropylamine in place of the equivalent amount of triethylamine. It is established that even after heating for 5 minutes the reaction has taken place to more than 95%. After a further 10 minutes the mixture is worked up analogously to the procedure described in Example 1. The yield of 2-ethylhexyl p-methoxycinnamate is 96% of theory.

Example 3

A mixture of 4.68 g (20 mmol) of p-iodoanisole, 4.05 g (22 mmol) of 2-ethylhexyl acrylate, 2.84 g (22 mmol) of 1,1,3,3-tetramethylbutylamine, 1.32 g (22 mmol) of acetic acid and 32 mg of palladium on charcoal (5%) is stirred at 150° C. for 3 hours. After working up as in Example 1 there is obtained 2-ethylhexyl p-methoxycinnamate in 92% yield.

Example 4

A mixture of 23.4 g (0.1 mol) of p-iodoanisole, 18.86 g (0.1025 mol) of 2-ethylhexyl acrylate, 8.76 g (0.12 mol) of diethylamine, 6.0 g (0.1 mol) of acetic acid and 130 mg of palladium on charcoal (5%) is stirred at 145° C. for 45 minutes. After the usual working up (see Example 1) 2-ethylhexyl p-methoxycinnamate is obtained in 86.6% yield.

Example 5

A mixture of 23.4 g (0.1 mmol) of p-iodoanisole, 22.1 g (0.12 mol) of 2-ethylhexyl acrylate, 1.5 g (0.025 mol) of acetic acid and 130 mg of palladium on charcoal (5%) in 6 ml of toluene is treated with 10.6 g (0.105 mol) of diisopropylamine at 140° C. within 15 minutes. After one hour the mixture is worked up as in Example 1. The yield of 2-ethylhexyl p-methoxycinnamate is 95.2% of theory.

Example 6

A mixture of 2.34 g (10 mmol) of p-iodoanisole, 2.57 g (10 mmol) of 2-ethylhexyl β-diethylamino-propionate, 0.9 g (15 mmol) of acetic acid and 15 mg of palladium on charcoal (5%) is stirred at 150° C. for 2 hours. Therafter, the mixture is worked up as in Example 1. 2-Ethylhexyl p-methoxycinnamate is obtained in 93% yield.

Example 7

A mixture of 2.34 g (10 mmol) of p-iodoanisole, 2.02 g (11 mmol) of 2-ethylhexyl acrylate, 1.42 g (11 mmol) of 1,1,3,3-tetramethylbutylamine and 16 mg of palladium on charcoal (5%) is stirred at 100° C. for one hour. According to gas chromatography there is also detected, in addition to unreacted p-iodoanisole and a trace of 2-ethylhexyl p-methoxycinnamate, 2-ethylhexyl (1,1,3,3-tetramethylbutylamino)propionate which, after adding 0.66 g (11 mmol) of acetic acid and increasing the temperature to 150° C., is converted in 3 hours into the desired 2-ethylhexyl p-methoxycinnamate. After the usual working up (see Example 1) the yield of 2-ethylhexyl p-methoxycinnamate is 92% of theory.

Example 8

A mixture of 2.34 g (10 mmol) of p-iodoanisole, 0.756 g (10.5 mmol) of acrylic acid, 0.803 g (11 mmol) of diethylamine and 16 mg of palladium on charcoal in 4 ml of dimethylformamide is stirred at 140° C. for 4 hours. Subsequently, the mixture is worked up by adding diethyl ether and 2N hydrochloric acid, washing the separated organic phase with water and subsequently drying over anhydrous sodium sulphate, concentrating the organic phase under reduced pressure and recrystallizing the solid residue from ethanol. In this manner there is obtained p-methoxycinnamic acid in 65% yield. M.p. 170° C. (no depression upon mixing with a pure sample of this acid); $^1$H-NMR (CDCl$_3$, 200 MHz): 3.85 ppm (s, 3H), 6.33 ppm (d, 15.5 Hz, 1H), 6.68–6.97 ppm (duplettoid, m 1H), 7.47–7.56 ppm (dupletteid m, 1H), 7.75 ppm (d, 15.5 Hz, 1H).

Example 9 a) 18.7 g (0.1 mole) p-bromoanisole, 500 mg Pd on carbon (5%), 40 ml N-methylpyrrolidone, 7.57 g (0.105 mole) acrylic acid and 13.57 g (0.105 mole) dibutylamine are stirred under nitrogen at 80° for 1 hour and then at 180° for 4 hours. The catalyst is removed by filtration at 100°. To the filtrate are added 200 ml of 2N sodium hydroxide and the solution is then washed twice with ether. Acidification to pH 1 with 2N hydrochloric acid, followed by filtration furnishes 10 g of p-methoxycinnamic acid (56% yield), top: 167°; no depression with an authentic sample is observed, the NMR data are as in example 8.

b) The above experiment was repeated with either potassium carbonate (0.1 mole) or sodium carbonate (0.1 mole) instead of dibutylamine. In both these cases, ether and sodium hydroxide were added prior to the filtration from the catalyst. No p-methoxycinnamic acid whatsover could be isolated in both cases.

I claim:

1. A process for the manufacture of a cinnamic acid derivative of the general formula

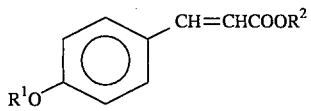

wherein

R$^1$ signifies hydrogen or C$_{1-8}$-alkyl and

R$^2$ signifies hydrogen, C$_{1-10}$-alkyl, C$_{1-10}$-hydroxyalkyl or C$_{1-4}$-alkoxy-C$_{1-10}$-alkyl, characterized by reacting a substituted benzene of the general formula

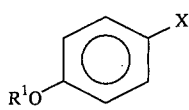

wherein R$^1$ has the significance given above, and X is iodine, or can also be bromine, when R$^2$ is hydrogen, with acrylic acid or an acrylic acid ester of the general formula

wherein R$^2$ has the significance given above, using a heterogeneous palladium catalyst and in the presence of the alkanoic acid ammonium salt formed from a C$_{2-5}$-alkanoic acid and a mono-, di- or trialkylamine of the general formula

wherein

R$^3$ and R$^4$ each independently signify hydrogen or C$_{1-10}$-alkyl and

R$^5$ signifies C$_{1-10}$-alkyl, or an optionally N-(C$_{1-4}$-alkyl)-substituted pyrrolidine, piperidine or morpholine (V), with the proviso that in the case of the manufacture of the cinnamic acid derivative of formula I in which R$^2$ signifies hydrogen the reaction can be carried out in the presence of the mono-, di- or trialkylamine of formula IV or of the optionally N-(C$_{1-4}$-alkyl)-substituted pyrrolidine, piperidine or morpholine (V) in place of the alkanoic acid ammonium salt defined above.

2. A process according to claim 1, characterized in that the substituted iodobenzene of formula II is p-iodoanisole.

3. A process according to claim 1, characterized in that 2-ethylhexyl acrylate is used as the compound of formula III.

4. A process according to claim 1, characterized in that the heterogeneous palladium catalyst is palladium on charcoal.

5. A process according to claim 1, characterized in that the C$_{2-5}$-alkanoic acid required for the formation of the alkanoic acid ammonium salt is acetic acid or propionic acid.

6. A process according to claim 1, characterized in that the amine IV or V required for the formation of the alkanoic acid ammonium salt is ethyldiisopropylamine, diethylamine, diisopropylamine or 1,1,3,3-tetramethylbutylamine.

7. A process according to claim 1, characterized in that the molar ratio of C$_{2-5}$-alkanoic acid to amine IV or V in the reaction mixture consisting of the reaction participants II and III, the C$_{2-5}$-alkanoic acid, the amine IV or V, the heterogeneous palladium catalyst and optionally solvent is about 1:1 to about 10:1.

8. A process according to any one of claims 1 to 6, characterized in that the amine IV or V is added relatively slowly to the reaction system, which consists of the reaction participants II and III, the C$_{2-5}$-alkanoic acid, the palladium catalyst and optionally solvent, such that finally the molar amount of added amine is in excess in comparison to the molar amount of C$_{2-5}$-alkanoic acid originally present in the reaction system.

9. A process for the manufacture of a cinnamic acid derivative of the general formula

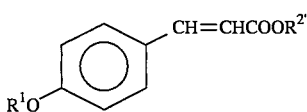

wherein

R$^1$ signifies hydrogen or C$_{1-8}$-alkyl and

R$^{2'}$ signifies C$_{1-10}$-alkyl, C$_{1-10}$-hydroxyalkyl or C$_{1-4}$-alkoxy-C$_{1-10}$-alkyl, characterized by reacting a substituted benzene of the general formula

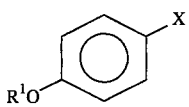

wherein R$^1$ and X have the significance given above, with the product of the Michael addition of an acrylic acid ester of the general formula

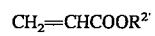

wherein R$^{2'}$ has the significance given above, with a primary or secondary amine of the general formula

wherein either

R$^8$ signifies hydrogen or C$_{1-10}$-alkyl and

R$^9$ signifies C$_{1-10}$-alkyl or

R$^8$ and R$^9$ together with the nitrogen atom to which they are attached signify pyrrolidino, piperidino or morpholino, using a heterogeneous palladium catalyst and in the presence of a C$_{2-5}$-alkanoic acid.

10. A process according to claim 1, characterized in that the process is directed to the manufacture of 2-ethylhexyl p-methoxycinnamate.

11. A process according to claim 1, wherein X in formula II is iodine.

* * * * *